(12) United States Patent
Montero Casimiro et al.

(10) Patent No.: US 8,563,003 B2
(45) Date of Patent: Oct. 22, 2013

(54) METHOD FOR THE TREATMENT OF MALIGNANT AND INFECTIOUS CHRONIC DISEASES

(75) Inventors: Jose Enrique Montero Casimiro, Cuidad Habana (CU); Rolando Perez Rodriguez, Cuidad Habana (CU); Agustin Bienvenido Lage Davila, Cuidad Habana (CU)

(73) Assignee: Centro de Inmunologia Molecular, Havana (CU)

( * ) Notice: Subject to any disclaimer, the term of this patent is extended or adjusted under 35 U.S.C. 154(b) by 992 days.

(21) Appl. No.: 10/309,015

(22) Filed: Dec. 4, 2002

(65) Prior Publication Data

US 2003/0104014 A1 Jun. 5, 2003

(30) Foreign Application Priority Data

Dec. 4, 2001 (CU) .......................................... 286/01

(51) Int. Cl.
*A61K 38/00* (2006.01)

(52) U.S. Cl.
USPC ................ 424/195.11; 424/184.1; 424/198.1; 530/350; 514/110; 514/449; 514/510

(58) Field of Classification Search
None
See application file for complete search history.

(56) References Cited

U.S. PATENT DOCUMENTS

| | | | | | |
|---|---|---|---|---|---|
| 5,597,798 | A | * | 1/1997 | Howell et al. | 514/7.6 |
| 5,728,707 | A | * | 3/1998 | Wehrmann | 514/274 |
| 5,894,018 | A | * | 4/1999 | Davila et al. | 424/195.11 |
| 6,080,399 | A | * | 6/2000 | Gajewski et al. | 424/85.2 |
| 6,277,368 | B1 | * | 8/2001 | Hiserodt et al. | 424/93.21 |

FOREIGN PATENT DOCUMENTS

| | | |
|---|---|---|
| WO | WO-88-00837 | 2/1988 |
| WO | WO-91-01146 | 2/1991 |
| WO | WO-91-09871 | 7/1991 |

OTHER PUBLICATIONS

Komenaka et al., Clinics in Dermatology, 2004, 22: 251-265.*
Evans et al., Q. J. Med 1999: 92: 299-307.*
Stevenson et al., Corr. Opin. Oncol., 2005, 17:573-577.*
Li et al., Curr. Pham. Design, 2005, 11:3501-3509.*
Gonzalez et al., Clinical Cancer Res. Nov. 6, 2000, supp. 467.*
Juma et al., Br. J. Clin. Pharmac., 1979, 8:209-217.*
Mackall et al., Blood, 1997, 89:3700-3707.*

"Induction of Immune Recognition of Self Epidermal Growth Factor (EGF): Effect on EGF-Biodistribution and Tumor Growth", G. Gonzalez, et al, Vaccine Research, vol. 5, No. 4, 1996, pp. 233-244.
"Induction of Immune Recognition of Self-Epidermal Growth Factor II: Characterization of the Antibody Response and the Use of a Fusion Protein", G. Gonzalez, et al. Vaccine Research, vol. 6, No. 2, 1997, pp. 91-100.
"A Novel Cancer Vaccine Omposed of Human-Recombiant Epidermal Growth Factor Linked to a Carrier Protein: Report of a pilot Clinical Trial", G. Gonzalez, et al., Annals of Oncology 9: 1998, pp. 431-435.
"T-Cell Immunodeficiency Following Cytotoxic Antineoplastic Therapy: A Review", C. Mackall, The Oncologist 1999; 4, pp. 370-378.
"Restoration of T-Cell Homeostasis after T-Cell Depletion", C. Mackall, et al, Immunology, vol. 9, 1997, pp. 339-346.
"Constraints on CD4 Recovery Postchemotherapy in Adults: Thymic Insufficiency and Apoptotic Decline of Expanded Peripheral CD4 Cells", F. Hakim, et al., Blood, vol. 90, No. 9, Nov. 1, 1997, pp. 3789-3798.
"Comparison of Antibody Titers After Immunization With Monovalent or Tetravalent KLH Conjugate Vaccines" G. Ragupathi, et al, Vaccine 2002, pp. 1030-1038.
Cohen, S. and Carpenter, G., "Human Epidermal Growth Factor: Isolation and Chemical and Biological Properties," PNAS USA 72(4):1317-1321 (1975).
Spiegel et al., "Gangliosides as biomodal regulators of cell growth," PNAS USA 84:141-145 (1987).
EP 94203576 Partial Search Report dated Aug. 9, 1996.

* cited by examiner

*Primary Examiner* — Sean E Aeder
*Assistant Examiner* — Julie Wu
(74) *Attorney, Agent, or Firm* — Rothwell, Figg, Ernst & Manbeck P.C.

(57) ABSTRACT

The present invention relates to methods of treatment useful in chronic diseases, by means of the rupture of tolerance to self-antigens and increasing autoimmune response against these antigens. More particularly, the present invention relates to methods useful in the treatment of tumors that are growth dependent on the Epidermal Growth Factor, including non-small cell lung carcinoma.
In the present invention a therapeutic combination is revealed that includes the combination of a vaccine against self antigens with a monoclonal antibody against peripheral T cells or a chemotherapeutic drug able to induce a depletion of peripheral T cells.
In another one of its aspects the present invention reveals a method of treatment of chronic diseases in which the rupture of the tolerance to self antigens is essential for the control of the disease, this method includes the administration of a immune suppressor agent between two cycles of vaccination against a self antigen, which could be for example the EGF, being this scheme of effective treatment for the reduction of tumors whose growth depends on EGF.

47 Claims, 4 Drawing Sheets

FIGURES
Figure 1-
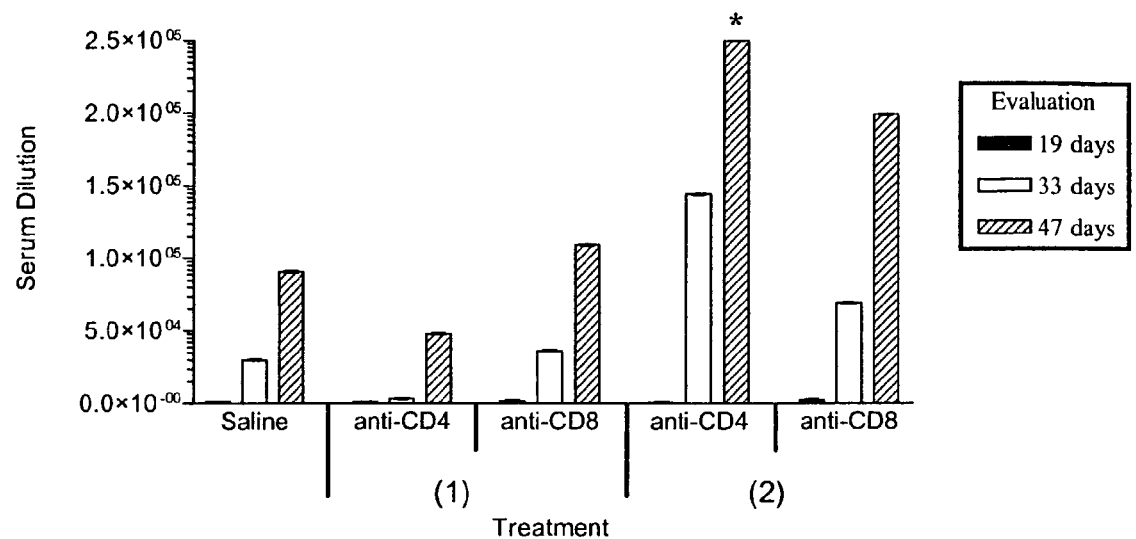
Figure 2-
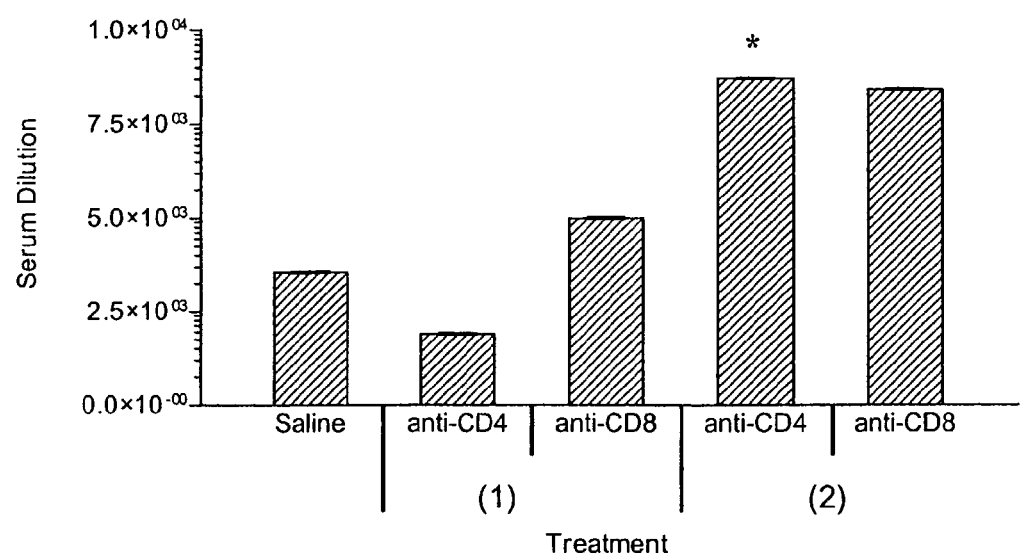

Figure 3-
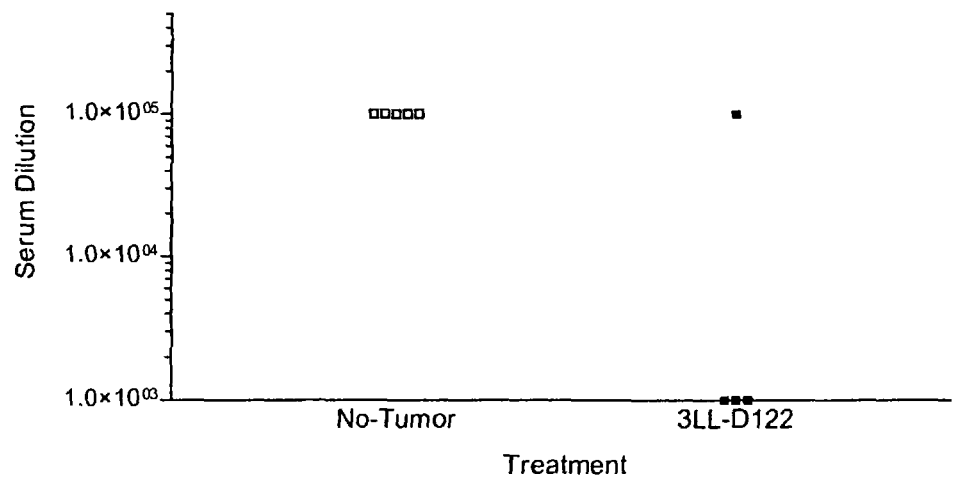
Figure 4:
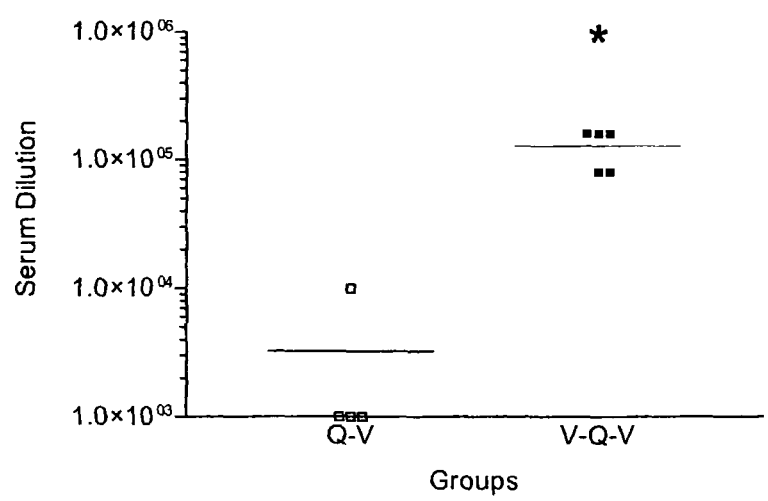

Figure 5-
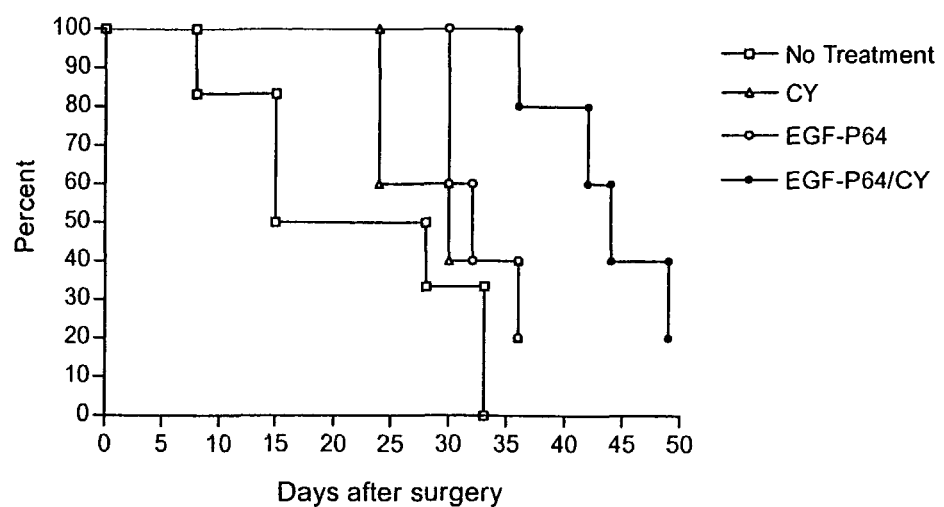
Figure 6-
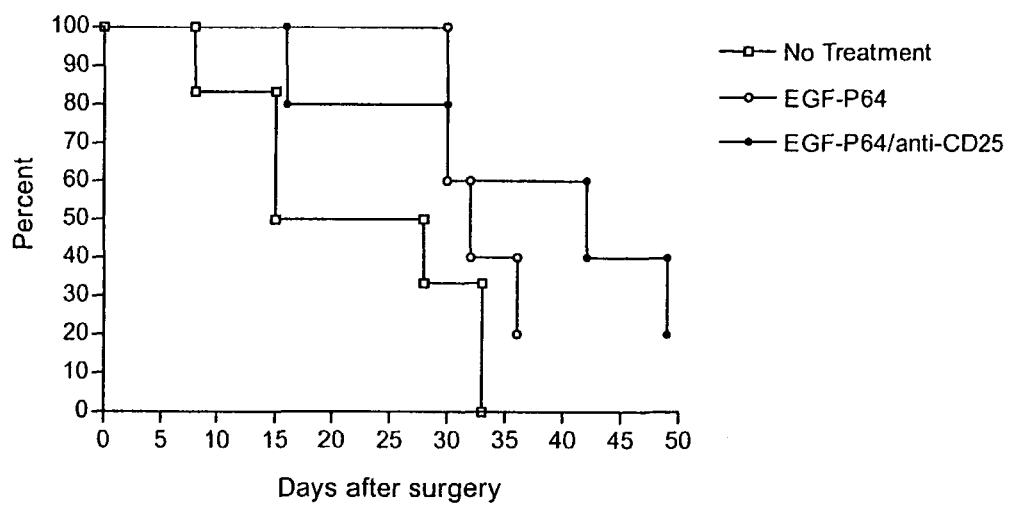

METHOD FOR THE TREATMENT OF MALIGNANT AND INFECTIOUS CHRONIC DISEASES

TECHNICAL FIELD

The present invention relates to methods of treatment useful in chronic diseases, by means of the rupture of tolerance to self-antigens and increasing autoimmune response against these antigens. More particularly, the present invention relates to methods useful in the treatment of tumors that are growth dependent on the Epidermal Growth Factor, including non-small cell lung carcinoma.

PRIOR ART

The cancer immunology is based on the premise of tumor-associated antigens, which are expressed by human tumors and not in normal tissues. An alternative to control the division and proliferation of the malignant cells has been to isolate these antigens and present them so that they are recognized by the immune system as non-self antigens and this way to induce a specific immune response. In spite of the several evaluations of this approach, most of the intents of inducing an effective tumoral regression in humans has not been successful. The poor induction of a specific immune response in cancer patients has been the main trouble.

Recently have been shown experimental dates that support the idea that the immune repertoire of cancer patients contains B and T cells that recognize the self-antigens expressed by the autologous tumor cells. Moreover, it has been established that deficiency of T cells or energy is not the reason for the growth of the antigenic tumor cells.

Most of the antigens expressed by tumor cells, they reflect the differentiation state of the normal counterpart in the same differentiation state. Accordingly, the self-antigens are emerging like target for cancer immunotherapy. With little success various candidates have been evaluated as much in experimental protocols as in clinical trials.

It is known in the state-of-the-art that self-antigens require adjutants as key element in the induction of immune response. Different composed they have been used for cancer in clinical trials using therapeutic vaccines based on these antigens. In this sense the therapeutic strategies have been limited to the activation of peripheral lymphocytes by an increase in the accessory molecules availability (cytokines, etc) or by the use of modified self antigens, structurally homologous molecules expressed in insects or infectious pathogens (viral vectors) as "a danger signal". Nevertheless this strategy in many cases does not increase substantially the immune response and in other cases it is abolished after the induction. Therefore the main problem to solve is the form to break the state of immune tolerance or what is same, the ignorance to the self-antigens contained in vaccines and this way to induce the tumor regression.

A variety of tumors exist whose proliferation depends on Epidermal Growth Factor (EGF). A strategy has been to use the active immunotherapy with vaccines that contain EGF to induce the immune response against this molecule and by this route to inhibit the proliferation effect of the EGF on these tumors. Generally these vaccines include an adjuvant in order to increase the specific immune response.

The EGF system has been target for the active immunotherapy specific for cancer. An example of it constitutes the use of a vaccine that contains one of the main ligands of the EGF-R, the EGF, linked to a carrier protein (U.S. Pat. No. 5,984,018). This vaccine is able to induce an antibody response specific against the autologous or heterologous EGF and to inhibit the binding to its receptor, being blocked mechanisms of proliferation triggered by this binding. Preclinical studies have shown that the immunization of mice with autologous or heterologous EGF linked to a carrier protein in adjuvant increase the survival of mice bearing the Ehrlich ascitic tumor (EAT) (González G. et al. (1996) Vaccine Research 5 (4): 233-243; González G. Et al. (1997) Vaccine Research 6 (2): 91-100)

Results in a Phase I clinical trial using a recombinant vaccine containing human EGF demonstrated the immunogenicity and the none-toxicity caused by the vaccination (González G. et al. (1998) Annals of Oncology): 1-5).

The cancer vaccine development represents an alternative to chemotherapy and together with radiotherapy constitutes the conventional weapons in the treatment of cancer. For example the treatment established for patients with lung carcinomas, an early therapy involves the administration of as much of radiations as of a combination of drugs like 5-Fu and Cisplatine among others.

For breast cancer, the treatment involves the administration of an antibody against the Her-2 receptor, like the Herceptin together with chemotherapy that can be Taxol. Nevertheless, combining specific active immunotherapy with chemotherapy has poor success, in this sense, lymphopenia in cancer patients induced by chemotherapy has been reported (Mackall C L. Oncologist 1999; 4(5):370-8; Mackall C L, Hakim F T, Gress R E. Semin Immunol 1997 December; 9(6):339-46; Hakim F T, Cepeda R, Kaimei S, Mackall C L, McAtee N, Zujewski J, Cowan K, Gress R E. Blood 1997 Nov. 1; 90(9): 3789-98.) The aim of many clinical trials using specific active immunotherapy in advanced cancer patients is to stabilize the objective clinical response induced by chemotherapy, in other words, responder patients are treated with a vaccination schema after chemotherapy (Shawler D L, Bartholomew R M, Garrett M A, Trauger R J, Dorigo O, Van Beveren C, Marchese A, Ferre F, Duffy C, Carlo D J, Sherman L A, Gold D P, Sobol R E. Clin Exp Immunol 2002 July; 129(1):99-106; Musselli C, Ragupathi G, Gilewski T, Panageas K S, Spinet Y, Livingston P O. Int J Cancer 2002 Feb. 10; 97(5):660-7; Ragupathi G, Cappello S, Yi S S, Canter D, Spassova M, Bommann W G, Danishefsky S J, Livingston P O. Vaccine 2002 Jan. 15; 20(7-8):1030-8; Holmberg L A, Sandmaier B M. Expert Opin Blot Ther 2001 September; 1(5):881-91).

Although a variety of anti cancer agents are used or in development is increasing, the cancer prevalence imposes the need to continue developing and improving the therapeutic arms against this disease.

DETAILED DESCRIPTION OF THE INVENTION

The invention is related to a therapeutic treatment of chronic diseases like cancer and chronic infectious diseases, in which immune system has an important role. The present invention includes the combination in said treatment of vaccines against self-antigens with immune modulators; immune modulators could be chemotherapy or monoclonal antibodies that have this effect on the immune system with a sequence of vaccination-immune modulation-vaccination (VIV). In a preferred embodiment the immune modulators are drugs currently used for chemotherapy, so the sequence must be vaccination-chemotherapy-vaccination (VQV, Spanish abbreviation) opposite to the current trend, which is to administer vaccination just after chemotherapy.

Thus, the method of treatment of the present invention comprises the following steps:

Immunizing a patient with a vaccine containing a self-antigen associated with said malignant or infectious chronic disease, being said self-antigen coupled to a carrier protein;

Treating said patient with an immune modulator agent; and finally

Immunizing said patient again with the vaccine of the initial step.

In a preferably embodiment of the invention the method includes a first immunization with a vaccine containing, as self antigen associated with said malignant or infectious chronic disease the EGF, which is used range between 50 and 250 μg per dose and it is coupled to the carrier protein p64K from *Neisseria meningitidis*. The vaccine also contains additionally an appropriate adjuvant selected from the group comprising aluminum hydroxide or Montanide ISA 51.

In the method of the invention a subject is treated with the vaccine by means of a vaccine cycle to raise titers of measurable serum antibodies until obtaining at least the double of the initial titer measured before beginning the immunizations, preferably three times and even more preferably at least higher than 4 times the initial titer.

In another preferably embodiment in this invention the method of treatment includes as immune modulator agent a monoclonal antibody raised against mammalian T cells, which is used in a concentration range between 0.5 to 100 mg per doses, and it is preferably an anti-CD25 monoclonal antibody.

Similarly as immune modulator agent can be used one or several chemotherapeutic drugs, which are employed in a range of concentration between 10 and 200 mg per Kg of body weight. Within these chemotherapeutic agents they are preferably selected Cyclophosphamide, 5 Fluoracil (5-FU), Taxol, Cisplatin and Adriamicin.

The method of the invention is particularly useful for the treatment of tumors of epidermoid origin, such as lung, breast and head and neck carcinomas.

In the treatment scheme that involves the administration of two compounds, they are administered as independent doses to the same patient in the course of the therapy.

The expression vaccines against self-antigens talks about to a useful agent for active immunotherapy so that it rise a measurable autoimmune response in the subject receiving the treatment, which recognizes the self antigen used for vaccination. The auto antibodies titers can be detected in serum by whichever of the methods available in the state-of-the-art for the measurement of auto antibodies or by detection of the specific immune response in peripheral blood, as much by measurement of specific antibodies as by measurement of specific T cells.

The vaccine used in the invention contains as self-antigen the autologous or heterologous EGF. The expression EGF vaccine talks about a useful agent to raise measurable titers of autoantibodies against the autologous or heterologous EGF in the subject receiving the vaccine.

The expression EGF talks about the Epidermal Growth Factor, a 53 amino acids polypeptide whose sequence has been reported by Cohen S., Proc. Natl. Acad. Sci. The USA 1975, 72 (1): 317. It also includes analogs and fragments of this molecule that when they are administered as a vaccine, it is able to raise in the receiving subject a particular EGF-vaccine response, as it is the increase of antibody titers against EGF in serum of patients.

Preferably the vaccine includes human EGF (hu-EGF). But more preferred this vaccine includes in addition to hu-EGF a carrier protein to increase the immune response in the receiving subject. Such carrier proteins can be among others tetanic toxoid, chain B of the cholera toxin, the protein p64 of the membrane protein complex of the *Neisseria meningitidis*, monoclonal antibodies or very small size proteoliposomes (VSSP) derivatives of the external membrane proteins of the *Neisseria meningitidis* bacterium, that contain powerful ligands of the innate immunity and gangliosides. Preferably the vaccine includes the self-antigens associated to VSSP.

The vaccine against EGF includes in the formulation in addition to the EGF and the carrier protein an adjuvant. Anyone of commercially available adjuvants could be used, including for example, aluminum hydroxide, QS 21 or Montanide ISA 51. In a preferred embodiment the vaccine contains EGF/p64 with Montanide ISA 51.

The vaccine against the EGF is suitably for parenteral administration. The administration route can be intra-dermic, subcutaneously or preferably by intramuscular route. Preferably the patient is treated with an immune modulator agent after one or more doses of vaccination and lastly, at the moment at which begins the regeneration of peripheral T cells the patient is reimmunized with the vaccine. Being that the response to the self-antigens is increased significantly.

The expression "immune modulators agent" talks about those molecules able to contribute or to facilitate a rupture of the tolerance to self-antigens in the subjects receiving the therapeutic combination. Preferably within them can be included monoclonal antibodies against mammalian T cells or chemotherapeutic agents to induce depletion of peripheral T cells. Monoclonal antibodies could be anti-CD4, anti-CD6, anti-CD8, anti-CD52, anti-CD25 among others, also could be used as immune modulators, chemotherapeutic agents as Cyclophosphamide, Cisplatin, Adriamicin and 5-FU (5 Fluoracil) and Taxol. In another embodiment of the present invention, as immune modulator agent can be used a mixture that contains several chemotherapeutic drugs.

In a preferred embodiment the therapeutic combination includes the treatment with cyclophosphamide and more preferably with an anti-CD25 monoclonal antibody. The immune modulator agent suitably formulated for its parenteral administration. The administration route can preferably be intra-peritoneal, oral or by intravenous route.

Actually, the subject is treated with the vaccine using a scheme of the suitable doses to raise titers of measurable serum antibodies, can be made repetitive administrations until obtaining the desired titers. Preferably the antibody titers are in relative terms, at least the double of the initial titer measured before beginning the immunizations; preferably the triple and even more preferably at least higher than 4 times. Expressed numerically in dilution terms, they must be at least 1 in 200, preferably 1 in 500 and even more preferably 1 in 1000.

In agreement with the present invention, the subjects receiving immunotherapy with the vaccine against self-antigens also are treated with immune modulator agents. As much the patients who suffer cancer or chronic infectious diseases are susceptible of the therapeutic combination disclosed in the present invention, where to break the tolerance of the immune system to self-antigens is very important. In a preferred embodiment of the present invention, cancer patients are treated with EGF vaccine combined with conventional chemotherapy available in the market, preferably cyclophosphamide.

The useful immune modulator treatment with the combination disclosed in the present invention can involve the administration of one or several chemotherapeutic drugs. In a preferred embodiment, the subject is treated with an anti-CD25 antibody. In a different embodiment the patient could be treated with cyclophosphamide.

In agreement with the therapeutic combination disclosed in the present invention, the immune modulator agent is administered between two vaccination cycles. Preferably the immune modulator is administered when measurable titers of antibodies against the self antigen in the serum of the patients are detected, at last and after the administration of the immune modulator agent another cycle of vaccination is administered, preferably this second cycle of vaccination will be administered at the moment in which the regeneration of T cells of the peripheral system begins, obtaining a significant increase of the antibody titers against the self antigen.

In a preferred embodiment, the therapeutic combination includes a vaccine whose active principle is the EGF, with the objective to raise auto antibody titers against this molecule, preferably EGF together with the protein p64 and an appropriate adjuvant, one that could be aluminum hydroxide or Montanide ISA 51. After the administration of one or more dose of the EGF/p64 vaccine, a dose of cyclophosphamide is administered and later another cycle of EGF/p64 vaccine is applied.

Preferably the immune modulator agent is administered when the antibody titer against EGF, measured in the serum of the patient, reveals an autoimmune response against the EGF after vaccination. In a preferred embodiment of the present invention, the patient bearing a tumor whose growth and proliferation are EGF depended, first is vaccinated with the EGF/p64 vaccine in one or more dose, until the expected antibody titers could be measured and then the patient is treated with immune modulators, the immune modulators can be a monoclonal antibody anti-T cells or a chemotherapy, with a conventional drug or a mix of those used for cancer treatment and that has a well-known immune modulator effect, this immune modulator treatment becomes in one or more dose until a depletion of peripheral T cells is obtained; later the patient is treated again with the EGF/p64 vaccine, this second cycle of vaccination begins preferably at the moment at which the regeneration of peripheral T cells begins, as a result a reduction of the volume and size of the tumor is obtained, consequently increased survival in the treated patients is observed.

The therapeutic combination of the present invention is useful in the treatment of the cancer and other chronic diseases like, the chronic infectious diseases, where it is important to break the tolerance of the immune system of the patient to self antigens.

In another aspect of the present invention a suitable range of dose of the immune modulator is provided to obtain the immune modulation of the patient immune system. Such doses of the immune modulator in the case of a monoclonal antibody are used in a range of 0.5-100 mg/dose, preferably 1 mg/dose, the chemotherapeutic drugs preferably in the range of doses that usually are used in the clinical practice, between 10-200 mg/Kg of weight.

The subjects that can be treated with the therapeutic combination of the present invention include mammals and particularly humans. Preferably the vaccine used in the present invention uses as active principle autologous or heterologous antigens in relation with the receptor subject.

With the therapeutic combination of the present invention an unexpected and significant increase of the levels of antibodies against self-antigens is obtained, and as a consequence the control of the disease by the immune system is achieved. Particularly in the treatment of EGF dependent tumors, the present therapeutic combination causes an increase of the titers of antibodies against the autologous or heterologous EGF which is higher than that obtained when the vaccine is used alone, this significant increase of the antibody titers is associated to a anti-tumor effect, expressed in terms of reduction of the volume and size of the tumor and with an increased survival.

EXAMPLES

Example 1

Comparison Between Two Treatment Schemes on the Induction of Antibodies Against Human EGF in Healthy Mice (VIV Vs IVV). Immune Modulating With Anti-Mammalian T Cells Antibodies The transitory immune modulation with anti-CD4 and anti-CD8 Monoclonal Antibodies increases the antibody response against Epidermal Growth Factor and it depends on the treatment scheme used.

BALB/c mice were immunized using two combined protocols: According to the scheme, (1) the mice were injected by intravenous route with a dose of 0.5 mg of anti-CD4 or anti-CD8 monoclonal antibodies (MAbs). Five days later mice were immunized by subcutaneous route with 50 µg of human Epidermal Growth Factor (hu-EGF) in Complete Freund Adjuvant, two weeks later, the mice were re-immunized by subcutaneous route with a second dose of 50 µg of hu-EGF in Incomplete Freund Adjuvant (IFA).

According to the scheme (2), the mice were injected by subcutaneous route with 50 µg of human Epidermal Growth Factor (hu-EGF) in Complete Freund Adjuvant and two weeks later treated by intravenous route with a dose about 0.5 mg of anti-004 or anti-CD8 monoclonal antibodies (Mabs). After five days the mice were re-immunized by subcutaneous route with a second dose of 50 µg of hu-EGF in Incomplete Freund Adjuvant (IFA). In FIG. 1 it is showed that the immune modulation with both MAbs anti-CD4 and anti-CD8 using the scheme (2) increases IgG antibody response against EGF, the one that was significantly higher than the response exhibited by the mice immunized twice with hu-EGF and treated with saline solution, which were used as control. It is shown the geometric average of the IgG antibody titers for each group at days 19, 33 and 47 after the first immunization.

Example 2

Comparison Between Two Treatment Schemes on the Induction of Antibodies Against Autologous EGF in Healthy Mice (VIV Vs IVV). Immune Modulating with Anti-Mammalian T Cells Antibodies The transitory immune modulation with anti-CD4 and anti-CD8 monoclonal antibodies increases the antibody response against the autologous Epidermal Growth Factor. BALB/c mice were immunized using two protocols combined similar to that described in Example 1 and the IgG antibody response against murine EGF (autologous) was measured. FIG. 2 shows that the immune modulation with both anti-CD4 and anti-CD8 Mabs using the scheme (2) also increases the of IgG antibody response against the murine EGF, the one that was significantly higher than the response exhibited by the mice immunized twice with hu-EGF and treated with saline solution, which were used as control. It is shown the geometric average of the IgG antibody titers for each group at day 47 after the first immunization.

Example 3

Tumor Effect on the Induction of an Antibody Response Against Vaccine Antigens The immune response against vaccine containing self-antigens diminishes by the presence of tumor in the immunized subjects.

C57BL/6 mice were injected by intramuscular route with a vaccine that contains 4 μg of human EGF conjugated to the P64 protein (EGF-p64) in Montanide ISA 51 (100 μl final volume) and two weeks later were re-immunized by intramuscular route with a second dose of said vaccine. A group of these animals was inoculated with the syngeneic tumor 3LL-D122 (200 000 cells/animal) in the right plantar pad 2 days previous to the first immunization.

FIG. 3 shows that the presence of the syngeneic tumor influences negatively in the induction of the immune response against the vacunal antigen. The individual titers of IgG+IgM antibodies are shown for each group day 47 after the first immunization.

Example 4

Induction of Higher Serum Titers Against Human EGF by Combining Immune Modulation with Poly Chemotherapy and Vaccination Immunization before poly chemotherapy treatment induces a higher immune response against vaccine antigens in mice bearing tumors.

C57BL/6 mice were injected with the syngeneic tumor 3LL-D122 (200 000 cells/animal) in the right plantar pad. The evolution of the tumor was evaluated by measurement of its diameters every 3 days.

Four weeks later, the surgery of the primary tumor was practiced (amputation) when it reached 8-9 mm of diameter, mice were treated with first-line conventional poly chemotherapy using Cyclophosphamide 600 mg/m$^2$ y Adriamicine 60 mg/m$^2$. After two weeks the animals were injected by intramuscular route with a vaccine that contains 4 ug of EGF conjugated with p64 protein (EGF-p64) in Montanide ISA 51 (100 μl final volume). A sub group of these animals received an additional vaccination cycle previous to poly chemotherapy treatment FIG. 4 shows that immunization previous poly chemotherapy (group V-Q-V) have a positive influence on the development of the immune response against vaccine antigen. It is shown individual IgG+IgM antibody titers for each group at day 59 after inoculation of the primary tumor.

Example 5

Inducing an Increase of the Survival in Animals Bearing Tumors by the Combination of Immune Modulation with Chemotherapy and Vaccination The combined treatment with immune modulators during immunization with vaccine antigens increase the survival of animals bearing tumors.

C57BL/6 mice were injected with the syngeneic tumor 3LL-D122 (200 000 cells/animal) in the right plantar pad. The evolution of the tumor was evaluated by measurement of its diameters every 3 days and surgery of the primary tumor was practiced (amputation) when it reached 8-9 mm of diameter. Mice survival, which is depended of spontaneous lung metastases was measured.

Two days after the inoculation of the tumor mice were injected by intramuscular route with a vaccine that contains 4 μg of human EGF conjugated to the p64 protein (EGF-p64) in Montanide ISA 51 (100 μl final volume) and two weeks later they were treated with 50 mg/kg of Cyclophosphamide by intravenous route or with saline solution. After three days, the mice were re-immunized by intramuscular route with a second dose of the EGF-p64 vaccine.

An animal group just was treated by intravenous route with 50 mg/kg of Cyclophosphamide and another one was not treated.

FIG. 5 shows that the immune modulation with Cyclophosphamide in the course of the vaccination increases the mice survival even in subjects bearing tumor, it was significantly higher than the response in mice immunized twice with the vaccine and treated with saline solution or in those that only were treated with Cyclophosphamide, both groups were used as control. It is shown the survival curves for each group after the surgery of the primary tumor.

Example 6

Inducing an Increase of the Survival in Animals Bearing Tumors by the Combination of Immune Modulation with Anti-Mammalian T Cells Antibodies and Vaccination C57BL/6 mice were injected with the syngenic tumor 3LL-D122 as it is described in Example 5.

Two days after to the inoculation of the tumor, mice were injected by intramuscular route with a vaccine that contains 4 μg of human EGF conjugated to the P64 protein (EGF-p64) in Montanide ISA 51 (100 μl final volume) and two weeks later they were treated with 1 mg of anti-CD25 monoclonal antibody by intravenous route or with saline solution as control. After three days, the mice were re-immunized by intramuscular route with a second dose of the EGF-p64 vaccine. An animal group did not receive any treatment.

FIG. 6 shows that a similar effect is obtained when Cyclophosphamide or anti-CD25 monoclonal antibody are used, enforcing the idea that the immune modulation in the course of the vaccination increases the survival of subjects bearing tumor, it was significantly higher than the survival of the immunized mice twice with the vaccine and treated with saline solution, groups which were used as control. It is shown the survival curves for each group after the surgery of the primary tumor.

Example 7

Comparison of the Effect of Two Treatment Schemes on the Metastases Occurrence in Mice Bearing Tumors. Immune Modulating with Anti-Mammalian T Cells Antibodies or Chemotherapy The combined treatment with immune modulators during immunization with vaccine antigens decrease occurrence of spontaneous lung metastases in animals bearing tumor.

C57BL/6 mice were injected with the syngeneic tumor 3LL-D122 (200 000 cells/animal) in the right plantar pad. The evolution of the tumor was evaluated by measurement of its diameters every 3 days and surgery of the primary tumor was practiced (amputation) when it reached 8-9 mm of diameter. Animals were sacrificed 21 days after the surgery of the primary tumor and metastases occurrence was measured.

Two days after the inoculation of the tumors mice were treated according to two different schemes.

First scheme: mice were injected with 50 mg/kg of Cyclophosphamide by intravenous route or with saline solution. Three days later mice were injected by intramuscular route with a vaccine that contains 7 µg of human EGF conjugated to the p64 protein (EGF-p64) in Montanide ISA 51 (100 µl final volume). After two weeks they ere re-immunized by intramuscular route with a second dose of the same vaccine Second scheme: mice were injected by intramuscular route with a vaccine that contains 7 µg of human EGF conjugated to the p64 protein (EGF-p64) in Montanide ISA 51 (100 µl final volume). After two weeks they were injected with 50 mg/kg of Cyclophosphamide or 1 mg of an anti-CD25 monoclonal antibody or with saline solution by intravenous route. Three days later mice were re-immunized with a second dose of EGF-p64 vaccine by intramuscular route.

FIG. 7 shows a significant decrease in the occurrence of spontaneous lung metastases when mice, bearing the highly metastasic tumor 3LL-D122, are treated using the second scheme even with chemotherapy or antibodies are used as immune modulators.

These effect was significantly superior to that obtained when mice were treated according the first scheme even with chemotherapy or antibodies. It is shown an average lung weight for each experimental group.

Example 8

Effect of the Treatment Schemes on a Cancer Patient

A patient of 62 years old that had a histologically confirmed Non Small Cell Lung Cancer (NSCLC) (Lung Adenocarcinoma) was selected for the trial. At moment of diagnosis, this patient had a lobectomy of the right Lung Superior Lobe. During 10 years, the patient remained disease free, with no respiratory symptoms.

After 10 years, patient suffered haemoptysis, asthenia, anorexia and weight loss. The imagenological methods (X-Rays and CT Scan) established the presence of multiple lesions in both lungs. The patient had a bronchoscopy that confirmed the metastatic origin of the lesions. The final diagnose was Metastatic Adenocarcinoma and consequently the prognosis was very poor.

A small tumor sample was evaluated for EGFR expression through an Immunohistochemical staining, which revealed a high membranous staining of about 80% of the tumor cells.

The patient received 5 doses of the EGF vaccine (EGF/P64) adjuvanted in Montanide ISA 51. The first 4 doses were administered weekly while the fifth dose was applied 30 days after the fourth vaccine. Afterward, patient started the chemotherapy regimen. The patient received 6 cycles of the following combination: Cisplatine (80 mg/m$^2$) and Navelbine (Vinorelbine) (30 mg/m$^2$).

Four weeks after finishing the oncospecific therapy, the patient continued receiving the EGF cancer vaccine. Reimmunization was done monthly thereafter.

The antibody response against the EGF has been measured since immunization begins.

The specific anti-EGF antibody titers are shown:

| | |
|---|---|
| Before vaccination | 1:500 |
| First month- | 1:2000 |
| Second month- | 1:32000 |
| Third month- | 1:16000 |
| Fourth month- | 1:16000 |
| Fifth month- | 1:8000 |
| Sixth month- | 1:8000 |
| Tenth month- | 1:8000 (before re-immunization) |
| Thirteenth month- | 1:16000 |

Before the chemotherapy regimen, the patient developed a very high antibody response (1:32000) after the use of the vaccine. During chemotherapy the antibody response decreased until 1:8000. During the tenth month, the antibody titers increased again up to 1:16000.

Fifteen months after the diagnose of the multiple metastases, this patient remains alive and the metastases on both lungs remain stable.

BRIEF DESCRIPTION OF THE FIGURES

FIG. 1: The transitory immune modulation with anti-CD4 and anti-CD8 monoclonal antibodies increases the antibody response against the human EGF and it depends on the treatment scheme. Y-axis represents serum dilution; X-axis corresponds to different treatment schemes. Bars correspond to the average value obtained for each animals group, asterisk means p<0.05.

FIG. 2: The transitory immune modulation with anti-CD4 and anti-CD8 monoclonal antibodies increases the antibody response against the autologous EGF. Idem to FIG. 1.

FIG. 3: The immune response against the self-antigen used for vaccination decreases in immunized subjects bearing tumors. Figure represents antibody values in serum for individual animals in each group.

FIG. 4: The vaccination before the poly chemotherapy treatment induces a higher immune response against self-antigens in immunized subjects bearing tumors. Figure represents antibody values in serum for individual animals in each group.

Figure 7:
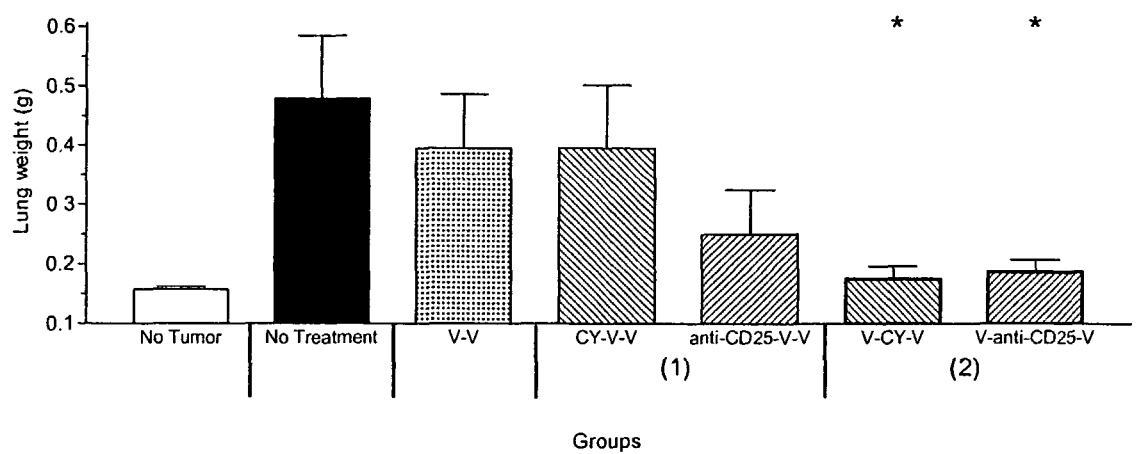

Q-V: the treatment scheme, chemotherapy followed by vaccination.

V-Q-V: the treatment scheme, chemotherapy between two vaccination cycles,

Asterisk p<0.05

FIG. 5: The treatment using immune modulators combined with immunization using cancer vaccines based on self-antigens increases survival of mice bearing tumors. Y-axis represents alive mice in %. Immune modulation using Cyclophosphamide (CY).

FIG. 6: The treatment using immune modulators combined with immunization using cancer vaccines based on self-antigens increases survival of mice bearing tumors. Y-axis represents alive mice in %. Immune modulation using anti-CD25 monoclonal antibody.

FIG. 7: The treatment using immune modulators combined with cancer vaccines based on self-antigens decreases occurrence of spontaneous lung metastases in mice bearing tumor. Y-axis represents the lung weight. X-axis represents different treatment schemes.

Bars correspond to the average weight for each group. Asterisk indicates p<0.05.

The invention claimed is:

1. A method of treating a human patient having a cancer consisting of administering active agents for the treatment of cancer to a human patient in need thereof, wherein the active agents consist of (i) a vaccine and (ii) an immune modulator agent;

wherein the vaccine consists essentially of a self antigen associated with said cancer and an adjuvant, wherein said self antigen is epidermal growth factor, wherein said epidermal growth factor is coupled to a carrier protein;

wherein the immune modulator agent is one or several chemotherapeutic agent(s); and further wherein the administration comprises the steps:
  (a) immunizing the human patient with 2-5 doses of the vaccine to raise the titers of measurable serum antibodies in the human patient to at least double the initial titer measured before beginning immunizations;
  (b) treating the human patient with 2-6 doses of the immune modulator agent to induce a transient depletion of peripheral T cells; and
  (c) immunizing the human patient again with monthly doses of the vaccine of step (a), wherein a first dose is administered when regeneration of the peripheral T cells begins,
  wherein the human patient having the cancer is treated.

2. The method according to claim 1 wherein the human patient is immunized with the with 2-5 doses of vaccine in step (a) to raise titers of measurable serum antibodies to at least three times the initial titer measured before beginning the immunizations, more preferably at least higher than 4 times the initial titer.

3. Method according to claims 1 or 2 wherein the vaccine containing the self antigen associated with said malignant or infectious chronic disease contains EGF coupled to the carrier protein p64K from Neisseria meningitidis and an appropriate adjuvant selected from the group comprising aluminum hydroxide or Montanide ISA 51.

4. A method according to claim 3 wherein the concentration of epidermal growth factor (EGF) in said vaccine is in the range between 50 and 250 µg per dose.

5. A method according to claim 1 wherein a chemotherapeutic agent is used in a concentration range between 10 and 200 mg per Kg of body weight.

6. A method according to claim 1 wherein a chemotherapeutic agent is cyclophosphamide.

7. A method according to claim 1 wherein a chemotherapeutic agent is 5 Fluoracil (5-FU).

8. A method according to claim 1 wherein a chemotherapeutic agent is Taxol.

9. A method according to claim 1 wherein a chemotherapeutic agent is Cisplatin.

10. A method according to claim 1 wherein a chemotherapeutic agent is Adriamycin.

11. A method according to claim 1 for the treatment of tumors of epidermoid origin.

12. A method according to claim 11 for the treatment of lung, breast, or head and neck carcinomas.

13. A method according to claim 1 wherein said self antigen is autologous or heterologous epidermal growth factor.

14. A method according to claim 1 wherein said self antigen is human epidermal growth factor.

15. A method according to claim 1 wherein said vaccine is administered to said subject by a parenteral administration selected from inter-dermic, subcutaneous and intramuscular administration routes.

16. A method of treating a human patient having a tumor consisting of administering active agents for the treatment of a tumor to a human patient in need thereof,
  wherein the active agents consist of (i) a vaccine and (ii) an immune modulator agent;
  wherein the vaccine consists essentially of a self antigen associated with said cancer and an adjuvant, wherein said self antigen is epidermal growth factor, wherein said epidermal growth factor is coupled to a carrier protein;
  wherein the immune modulator agent is one or several chemotherapeutic agent(s); and
  further wherein the administration comprises the steps:
    (a) immunizing the human patient with 2-5 doses of the vaccine to raise the titers of measurable serum antibodies in the human patient to at least double the initial titer measured before beginning immunizations;
    (b) treating the human patient with 2-6 doses of the immune modulator agent to induce a transient depletion of peripheral T cells; and
    (c) immunizing the human patient again with monthly doses of the vaccine of step (a), wherein a first dose is administered when regeneration of the peripheral T cells begins,
    wherein the human patient having the tumor is treated.

17. The method according to claim 16 wherein the human subject is immunized with the with 2-5 doses of vaccine in step (a) to raise titers of measurable serum antibodies to at least three times the initial titer measured before beginning the immunizations, more preferably at least higher than 4 times the initial titer.

18. The method according to claim 16 wherein the carrier protein is p64K from *Neisseria meningitidis* and wherein the adjuvant is aluminum hydroxide or Montanide ISA 51.

19. The method according to claim 17 wherein the carrier protein is p64K from *Neisseria meningitidis* and wherein the adjuvant is aluminum hydroxide or Montanide ISA 51.

20. A method according to claim 16 wherein the concentration of epidermal growth factor (EGF) in said vaccine is in the range between 50 and 250 µg per dose.

21. A method according to claim 16 wherein a chemotherapeutic agent is used in a concentration range between 10 and 200 mg per Kg of body weight.

22. A method according to claim 16 wherein a chemotherapeutic agent is cyclophosphamide.

23. A method according to claim 16 wherein a chemotherapeutic agent is 5 Fluoracil (5-FU).

24. A method according to claim 16 wherein a chemotherapeutic agent is Taxol.

25. A method according to claim 16 wherein a chemotherapeutic agent is Cisplatin.

26. A method according to claim 16 wherein a chemotherapeutic agent is Adriamycin.

27. A method according to claim 16 for the treatment of tumors of epidermoid origin.

28. A method according to claim 27 for the treatment of lung, breast, or head and neck carcinomas.

29. A method according to claim 16 wherein said self antigen is autologous or heterologous epidermal growth factor.

30. A method according to claim 16 wherein said self antigen is human epidermal growth factor.

31. A method according to claim 16 wherein said vaccine is administered to said subject by a parenteral administration selected from inter-dermic, subcutaneous and intramuscular administration routes.

32. A method of treating a human patient having a metastasis consisting of administering active agents for the treatment of metastasis to a human patient in need thereof,
  wherein the active agents consist of (i) a vaccine and (ii) an immune modulator agent;
  wherein the vaccine consists essentially of a self antigen associated with said cancer and an adjuvant, wherein said self antigen is epidermal growth factor, wherein said epidermal growth factor is coupled to a carrier protein;

wherein the immune modulator agent is one or several chemotherapeutic agent(s); and further wherein the administration comprises the steps:
(a) immunizing the human patient with 2-5 doses of the vaccine to raise the titers of measurable serum antibodies in the human patient to at least double the initial titer measured before beginning immunizations;
(b) treating the human patient with 2-6 doses of the immune modulator agent to induce a transient depletion of peripheral T cells; and
(c) immunizing the human patient again with monthly doses of the vaccine of step (a), wherein a first dose is administered when regeneration of the peripheral T cells begins, wherein the human patient having the metastasis is treated.

33. The method according to claim 32 wherein the human subject is immunized with the with 2-5 doses of vaccine in step (a) to raise titers of measurable serum antibodies to at least three times the initial titer measured before beginning the immunizations, more preferably at least higher than 4 times the initial titer.

34. The method according to claim 32 wherein the carrier protein is p64K from *Neisseria meningitidis* and wherein the adjuvant is aluminum hydroxide or Montanide ISA 51.

35. The method according to claim 33 wherein the carrier protein is p64K from *Neisseria meningitidis* and wherein the adjuvant is aluminum hydroxide or Montanide ISA 51.

36. A method according to claim 32 wherein the concentration of epidermal growth factor (EGF) in said vaccine is in the range between 50 and 250 µg per dose.

37. A method according to claim 32 wherein a chemotherapeutic agent is used in a concentration range between 10 and 200 mg per Kg of body weight.

38. A method according to claim 32 wherein a chemotherapeutic agent is cyclophosphamide.

39. A method according to claim 32 wherein a chemotherapeutic agent is 5 Fluoracil (5-FU).

40. A method according to claim 32 wherein a chemotherapeutic agent is Taxol.

41. A method according to claim 32 wherein a chemotherapeutic agent is Cisplatin.

42. A method according to claim 32 wherein a chemotherapeutic agent is Adriamycin.

43. A method according to claim 32 for the treatment of metastases of epidermoid origin.

44. A method according to claim 43 for the treatment of lung, breast, or head and neck carcinomas.

45. A method according to claim 43 wherein said self antigen is autologous or heterologous epidermal growth factor.

46. A method according to claim 32 wherein said self antigen is human epidermal growth factor.

47. A method according to claim 32 wherein said vaccine is administered to said subject by a parenteral administration selected from inter-dermic, subcutaneous and intramuscular administration routes.

* * * * *